(12) United States Patent
Ghosh et al.

(10) Patent No.: US 8,252,359 B2
(45) Date of Patent: Aug. 28, 2012

(54) METHOD FOR THE PREPARATION OF REFRESHING DRINK AND USE THEREOF

(75) Inventors: Pushpito Kumar Ghosh, Gujarat (IN); Maheshchandra Rameshchandra Rajyaguru, Gujarat (IN); Jinalal Sambhubhai Patolia, Bhavnagar (IN); Karuppanan Eswaran, Gujarat (IN); Subbarao Peddivenkata, Gujarat (IN); Mukesh Tribhovanbhai Shah, Gujarat (IN); Sudhakar Tukaram Zodape, Gujarat (IN); Sharda Vitthaldas Joshi, Gujarat (IN); Alamuru Venkata Rami Reddy, Gujarat (IN); Chhaganlal Vitthaldas Devmurari, Gujarat (IN); Sibdas Bandyopadhyay, West Bengal (IN); Ganesh Chandra Sahoo, West Bengal (IN)

(73) Assignee: Council of Scientific & Industrial Research, New Delhi (IN)

( * ) Notice: Subject to any disclaimer, the term of this patent is extended or adjusted under 35 U.S.C. 154(b) by 540 days.

(21) Appl. No.: 11/891,763

(22) Filed: Aug. 13, 2007

(65) Prior Publication Data
US 2008/0124429 A1  May 29, 2008

(30) Foreign Application Priority Data
Aug. 14, 2006 (IN) .......................... 1824/DEL/2006

(51) Int. Cl.
*A23L 2/00* (2006.01)
(52) U.S. Cl. ......... 426/590; 426/486; 426/487; 426/521
(58) Field of Classification Search ........................ None
See application file for complete search history.

(56) References Cited

U.S. PATENT DOCUMENTS

| 4,933,197 | A | * | 6/1990 | Walker et al. | 426/330.5 |
| 5,242,595 | A | * | 9/1993 | Morgart et al. | 210/636 |
| 6,022,573 | A | * | 2/2000 | Hagiwara | 426/270 |
| 6,573,250 | B2 | * | 6/2003 | Umeda et al. | 514/54 |
| 2004/0031302 | A1 | * | 2/2004 | Eswaran et al. | 71/23 |
| 2006/0263454 | A1 | * | 11/2006 | Sugiyama et al. | 424/729 |

FOREIGN PATENT DOCUMENTS

JP 2003144102 * 5/2003

OTHER PUBLICATIONS

Santoso, "Mineral Contents of Indonesian Seaweeds and Mineral Solubility Affected by Basic Cooking" 2006, Food. Sci. Technol. Res 12(1) pp. 59-66.*
Fayaz et al. "Chemical Composition, Iron Bioavailability, and Antioxidant, Activity of Kappaphycus alvarezzi (Doty)" J Agric. Food Chem. 2005 vol. 53, pp. 792-797.*

* cited by examiner

*Primary Examiner* — Humera Sheikh
*Assistant Examiner* — Felicia King
(74) *Attorney, Agent, or Firm* — Abelman, Frayne & Schwab

(57) ABSTRACT

The present invention discloses a nutritious, tasty and affordable drink made from the sap of *Kappaphycus alvarezii* seaweed which is readily cultivable. The drink resembles coconut water in appearance and taste and is rich in potassium. It also contains an adequate proportion of the daily requirement of iodine besides many other useful minerals such as magnesium, calcium, sodium, zinc, phosphorous and iron while having low concentrations of toxic elements such as lead and chromium. The process of refining sap, which enables the seaweed drink to be palatable and widely acceptable, besides bestowing adequate shelf life, is also described. The process of preparation is integrated with preparation of carrageenan and plant nutrient thereby making optimum use of the seaweed and minimizing waste.

4 Claims, No Drawings

METHOD FOR THE PREPARATION OF REFRESHING DRINK AND USE THEREOF

FIELD OF INVENTION

The present invention relates to a refreshing and tasty drink free from fishy odour obtained from *Kappaphycus alvarezii*.

More particularly, the present invention relates to the use of the sap obtained from *Kappaphycus alvarezii* as a material for the refreshing, tasty and nutritious drink.

Further, the present invention also provides a process for the preparation of a refreshing and tasty drink from *Kappaphycus alvarezii*.

BACKGROUND AND PRIOR ART OF THE INVENTION

Increased health consciousness and modern lifestyle has spurred the demand for foods and drinks with greater nutrition value which are also enjoyable to drink.

Reference is made to the report by Richards-Rajadurai (Richards-Rajadurai (1990) in RAS/90/002.FAO/UNDP Seafarming Project, Philippines.149-180) wherein, according to FAO, over 30 countries around the world harvest annually about 3.1 to 3.8 million tons wet weight of seaweeds Of this total, half of the quantity is utilized for human consumption and the rest for the production of industrially important phycocolloids such as agar, carrageenan and alginates.

Reference may be made to Chapman, V. J. & Chapman, D. J. (1980), *Seaweeds and their Uses*, Chapman & Hall, London, wherein details are provided of a wide variety of seaweeds and their uses. Several seaweed extracts are also reported to be useful as foliar spray for improved plant growth.

Reference may be made to the article by Critchley, A. T. (1993) (*Seaweed Cultivation and Marine Ranching*, M. Ohno and A. T. Critchley (eds), Kanagawa International Fisheries Training Center, Japan International Co-operation Agency, Yokosuka, Japan. pp 1-6) wherein the main types of edible seaweeds listed are *Laminaria, Undaria, Porphyra* and *Monostroma*. In Far East Countries (Japan, China, Philippines, Indonesia and Korea) seaweeds are abundantly used as nutritious foods/supplements and have become an important part of their national diet. In particular, *Porphyra* (popularly known as nori), *Laminaria* (kombu) and *Undaria* (wakame) are especially popular and consumed in large quantities.

Like vegetables, seaweeds contain all types of vitamins and antioxidants, including superoxide dismutase and ascorbic acid. Seaweeds are richer in group B vitamins—particularly B12—than their vegetable counterparts. Vitamin A content of seaweeds amounts to half of that in spinach. Dried sheets of *Porphyra* contain vitamin C in higher proportion than found in raw oranges ((Nisizawa et al., *Hydrobiologia* 151/152, 1987, 5-29).

Reference may be made to the article entitled "*Sea Vegetables for Food and Medicine*" by Ryan Drum (www.ryandrum.com/seaxpan1.html). It is stated therein that seaweeds are best used as regular components of a wise diet. Sea vegetables have been consumed regularly by all coastal peoples since the first days. Special harvesting, processing, storage, and eating rituals evolved to meet local needs. The ease of drying sea vegetables in full sunlight, and, their innate long-term stability when kept completely dry permits safe long-term storage and facilitates both personal and commercial transport, And, an almost indefinite shelf-life when stored completely dry and away from light. The article further states that while all seaweeds are edible, many are unpalatable. Reference is also made in the same article to algal drinks such as "Irish moss".

Reference is made to the article entitled "Evaluation of the taste and smell of bottled nutritive drinks" by Kataoka et al. (*Int. Jour. of Pharmaceutics,* 305, 2005, 13-21) wherein it is disclosed that overall palatability of drinks is positively correlated with sourness intensity and fruitiness and negatively correlated with bitterness intensity and the taste of medicinal plants. It is further stated that sourness and bitterness intensity could be predicted by taste sensor whereas fruitiness could be predicted by odor sensor, and that taste sensor and odor sensor are jointly useful in evaluating palatability of a drink.

Reference is made to JP60102179 wherein the preparation of a drink from seaweed is disclosed by T. Naoki. The drink is claimed to have high contents of protein, peptide, amino acid, polysaccharide, inorganic salt, etc. having high nutritive value free from unpleasant characteristic smell of seaweed, and is prepared by hydrolyzing seaweeds such as *Nemacystus decipiens* with large volumes (10-60 times) of acid or alkali at 100-110° C. for 5-12 h and adding a sweetener or sour seasoning to the hydrolysate solution. The main drawback is that large volumes of acid and alkali are required in the process. Moreover, such drinks are likely to be costly since a sole product is derived from the seaweed. No mention is made of the use of seaweed sap directly for the preparation of drink.

Reference is made to U.S. Pat. No. 6,573,250 wherein Umeda et al. have disclosed the preparation of food or beverage containing fucoidan. prepared from seaweed extract wherein the smell of seaweed is effectively removed with active carbon.

Reference may be made to U.S. Pat. No. 4,328,118 wherein the processing of algae in its natural wet state is described. No mention is made therein of any application as a drink.

Reference is made to U.S. Pat. No. 4,581,233 wherein it is disclosed by Herve et al. that the protoexoplasma of seaweed by a process wherein algae are deep-frozen and thereafter subjected to a cryogrinding (using for example two grinders in series under liquid nitrogen) and then to a rolling operation (with, for example, a cylinder machine) and finally to a homogenization operation. A "mother pulp" is thus obtained of which the constituent particles are approximately between 6 and 20.mu. Said mother pulp is also called "algae cream". The said mother pulp can be caused to pass over a decanter at high speed, giving thus two products, on the one hand, the solid part or cake which is called "algae base" and, on the other, the decanted liquor or juice which is called "protoexoplasma of algae". It is claimed that the protoexoplasma of *Ascophyllum Nodosum* can increase the gamma.-globulin level in human beings.

Reference may also be made to JP64002562 wherein Y. Sadao has disclosed the preparation of a liquid drink and solid food beneficial for health and suitable as a tonic, by crushing aloe, seaweed, garlic, etc., fermenting in a liquid mixture of alcohol, whole rice vinegar, etc., and filtering the product to obtain a transparent liquid drink. No mention is made of the use of seaweed sap directly for the preparation of drink. Moreover, the use of alcohol may not be acceptable to many consumers besides the fact that the product involves too many components.

Reference may be made to the preparation of novel health food and drink containing marine algae by Hagino Hiroshi and Sato Shiho in US2005217596 wherein the use of marine algae powder prepared from *Porphyra* and Undaria is disclosed. It is claimed therein that the abundant nutritional ingredients and health functional ingredients of these seaweeds is preserved in the granules while the odor contained in the marine algae is effectively abated or reduced. No mention is made of the use of plant sap directly for preparation of drink.

Reference may be made to a seaweed jelly drink by the name of agar alouda sold in Mauritius.

Reference may be made to an article entitled "Jamaican café spices things up" published in the Oct. 2, 2002 issue of Seacoastonline wherein a seaweed drink by the name of Irish Moss is described. The drink is reported to taste like eggnog.

Reference may be made to the article entitled "Kelpie Seaweed Ale" (www.bostonphoenix.com/boston/food_drink/noshing/documents/02556527.htm) wherein it is stated that 500 mL of a seaweed drink by the name of Kelpie is sold for USD4.95.

Reference may be made to a seaweed drink sold by Repechage (www.repechage.com) which presumably assists in overcoming fatigue. 15 tubes of 10 mL each are sold for USD37.00.

Although it is well known that seaweeds can yield nutritional products such products tend to be quite costly since these products have to bear the entire seaweed cost when the seaweed is utilized for the sole purpose of that product. It would be highly desirable to make nutritional products from seaweeds more affordable, ideally by producing such products from any seaweed by-products that can be obtained in large volumes.

The red seaweed, *Kappaphycus alvarezii*, which grows in tropical waters, is cultivated extensively in countries such as the Philippines and Indonesia as a source of κ-carrageenan. J. G. Lewis, N. F. Stanley and G. G. Guist, in the book, *Algae and Human Affairs*, C. A. Lembi and J. R. Waaland, Eds., Cambridge University Press, Cambridge, 1990; pp. 218), have reviewed the diverse applications of refined and semi-refined κ-carrageenan. G. H. Thirkelsen (in: *Industrial Gums—Polysaccharides and their Derivatives*, R. L. Whistler and J. N. BeMiller, Eds., 3$^{rd}$ Edition, Academic Press Inc., New York, 1993, pp 145-180) has also described the diverse applications of carrageenan. κ-Carrageenan is used as a thickening agent in numerous applications such as pet food, fruit jam, toothpaste, and ice cream. No mention is made of any drink prepared from the seaweed.

Reference is made to the article by M. Fayaz et al. entitled "Chemical composition, iron bioavailability and antioxidant activity of *Kappaphycus-Alvarezzi* (DOTY)" (*Journal of Agricultural and Food Chemistry*, 53[3] (2005) 792-797), wherein some of the nutritional aspects of the *Kappaphycus alvarezii* seaweed have been discussed. However the studies were conducted on dry seaweed and no reference is made to the preparation of any drink either from the whole plant or from the sap.

It is known that potassium salt—a mineral found in many fruits, vegetables and legumes such as dried peas and beans—may protect against high blood pressure. Presence of potassium in low sodium salt inhibits sodium-induced hypertension. Reference may be made to "The Heinz Handbook of Nutrition" by Benjamin T. Burton, published for H. J. Heinz Co., by McGraw Hill Book Co., second edition, page 132-133, wherein it is mentioned that the dietary need for potassium roughly equals that of sodium. It is also stated that muscular weakness, increased nervousness and irritability, mental disorientation and cardiac irregularities manifest potassium deficiency. Many people, especially in poorer countries, do not have access to sufficient amounts of fresh fruits and vegetables with the result that their dietary needs of potassium have to be met by alternative means.

Reference may be made to the paper by Adhikary et al. entitled "Deacidification of Fruit Juices by Electrodialysis—Part II" (*Ind. J. Technol.* 25, 1987, 24-27) wherein it is reported that grape, pineapple and orange juices have 3173 ppm, 1500 ppm and 3150 ppm KCl, respectively whereas the NaCl concentrations are very low (<100 ppm) in all the cases. KCl, therefore, is an important nutrient provided by fruit juices but poor people in many countries cannot afford such juices.

Reference is made to US Pre-grant publication No: 2005/0220975A1 and PCT Application No: PCT/IB 04/03678 wherein Ghosh et al. have disclosed the preparation of low sodium salt of botanic origin through use of halophytic plants which are rich in NaCl and *Kappaphycus alvarezii* seaweed which is rich in KCl. The dried seaweed is thrashed to yield a salt which is largely KCl and can be refined for the purpose of producing low sodium salt. No mention is made of preparation of health drink from the seaweed.

Reference may be made to any standard reference book on the subject of iodine wherein the importance of iodine as a micronutrient is discussed. It is stated that the daily requirement of iodine varies from 50-150 µg/day which iodine can be provided in various forms such as in the form of iodized salt, iodine rich animal and plant products, and in the form of iodinated water (http://www.extention.umn.edu/, University of Minnesota Extension Service home page). Seaweeds are a particularly rich source of iodine ((Mairh et al. 1989, *Phytochemistry* 28 (12), 3307-3310) which helps in prevention of iodine deficiency disorders but care must be taken to ensure that seaweeds do not deliver excessive quantities of iodine.

Reference may be made to the article by T. Cooke entitled "Heavy Metals, Water and Health" (www.envirotechpubs.com/articles/iet200511_040.pdf) wherein the permitted levels of certain toxic heavy metals (antimony, 5 ppb; arsenic, 10 ppb; cadmium, 5 ppb; chromium, 50 ppb; lead, 10 ppb; mercury, 1 ppb) in European drinking water are provided.

Reference is made to U.S. Pat. No. 6,893,479 wherein the integrated method for production of kappa carrageenan and liquid plant nutrient from fresh *Kappaphycus alvarezii* seaweed has been disclosed by Eswaran et al. In this method the freshly harvested seaweed—which contains more than 90% by weight of water—is liquefied through a shearing action and the resultant slurry is filtered to yield the plant sap and a residue containing all of the kappa carrageenan originally present in the seaweed. The sap, which is obtained as by-product in up to 80% of the fresh weight of the plant, contains high concentrations of KCl as well as inorganic micronutrients and also contains useful organic nutrients which show beneficial effects on plant growth. No mention is, however, made of preparation of health drink from the sap or of its potential use for this purpose.

OBJECTS OF THE INVENTION

The main object of the present invention is to provide a refreshing and tasty drink free from fishy odour obtained from *Kappaphycus alvarezii*.

Another object of the present invention is to provide a process for the preparation of a refreshing and tasty drink Further, another object of the present invention is to provide the use of the sap obtained from *Kappaphycus alvarezii* as a material for the refreshing, tasty and nutritious drink Yet another object of the present invention is to provide a refreshing and tasty drink that can provide a substantial portion of the daily requirement of several essential micronutrients including iodine.

Yet another object of the present invention is to provide a refreshing and tasty drink with different flavors to suit different tastes through blending of the purified sap with other drinks or through incorporation of ingredients such as salt, lime, herbs, spices, carbon dioxide, etc.

SUMMARY OF THE INVENTION

The present invention deals with a nutritious and refreshing drink from the sap of *Kappaphycus alvarezii* seaweed wherein the sap is expelled from the fresh seaweed by mechanical action as reported in the prior art and preserved with food grade chemical preservatives or other forms of preservation. The sap, which is rich in potassium and several micronutrients including iodine, is clarified by physical means such as centrifugation or by chemical means such as addition of flocculants. The sap is then further treated with charcoal or passed through a carbon filter and thereafter subjected to polymeric or ceramic membrane filtration to obtain a colorless liquid that is free from any fishy or other unpleasant odour/taste. This purified sap is packed and stored till it is ready for consumption and at the time of serving it is diluted with appropriate volume of sweetened water whereupon the taste resembles to some extent the taste of tender coconut water.

DETAILED DESCRIPTION OF THE INVENTION

Accordingly, the present invention provides the use of the sap obtained from *Kappaphycus alvarezii* disclosed in U.S. Pat. No. 6,893,479, wherein the said drink containing the following ingredients:
  a) 2500-5000 mg/L potassium, 1000-2000 µg/L iodine and other essential minerals selected from the group comprising of 150-200 mg/L sodium, 750-1250 mg/L magnesium, 250-350 mg/L calcium, 25-35 mg/L phosphorous, 50-100 mg/L iron, 3-6 mg/L zinc, and 1.5-2.5 mg/L manganese;
  b) 0.75-1.0 g/L protein, 15-25 g/L carbohydrate, 0.2-0.3 ppm thiamine, 0.1-0.2 ppm riboflavin and only traces of fat with total energy content of 70-100 Kcal/L;
  c) <6 µg/L lead and <40 µg/L chromium.

In an embodiment of the present invention, the said sap is useful for the preparation of refreshing and tasty drink.

In another embodiment of the present invention, the said sap is able to fulfill the daily requirement of several essential micronutrients selected from the group comprising of potassium, iodine, sodium, magnesium, calcium, phosphorous, iron, zinc, and manganese. Further, the present invention also provides a method for the preparation of a refreshing and tasty drink from *Kappaphycus alvarezii*, wherein the said process comprising the steps of:
  a) providing sap from *Kappaphycus alvarezii* disclosed in U.S. Pat. No. 6,893,479;
  b) optionally adding the preservatives to the sap obtained from step (a);
  c) treating the sap obtained from step (a) or step (b) with activated charcoal powder or carbon filter to remove fishy odor and improve palatability;
  d) subjecting the sap obtained from step (c) to membrane filtration to remove colloidal impurities followed by sterilization to separate out all invisible microorganisms and to get the desired drink.
  e) optionally adding other commercially available drink, flavors or ingredients selected from the group comprising of salt, lime, herbs, spices, carbon dioxide etc to the drink obtained from step (d) through blending to enhance the taste of the drink In an embodiment of the present invention, the *Kappaphycus alvarezii* used is cultivated on rafts in the coastal areas of Tamil Nadu and Gujarat, India.

In another embodiment of the present invention, the preservatives used are selected from the group comprising of benzoic acid, potassium benzoate, sodium benzoate, methyl paraben and propyl paraben either alone or in combination wherein the concentration of the preservatives used in the range of 0.2-0.4% (w/v).

Further, in another embodiment of the present invention, the membrane used for filtration is selected from the group comprising of polysulfone ultrafiltration membrane of 200-300 kilo Dalton cut off operating at 4 kg/cm$^2$ pressure or 19-channel ceramic microfiltration element operated at 1 kg/cm$^2$ pressure.

In yet another embodiment of the present invention, the sterilization is carried out using heat, radiation or ozonolysis.

In still another embodiment of the present invention, the by-product retentate stream obtained after membrane filtration is useful as plant nutrient.

In still another embodiment of the present invention, the said drink is prepared by diluting the said sap with 2-4 parts of water containing additives selected from the group comprising of salt, sugar, lemon, carbon dioxide, etc.

In still another embodiment of the present invention, the said drink is prepared from refined sap resembles coconut water in appearance, aroma and taste when the it is diluted with 3 parts of water containing 4-6% (w/v) sucrose and preferably served in chilled condition.

In still another embodiment of the present invention, the packed sap or drink can be stored under ambient conditions but more preferably under refrigerated conditions at a temperature of 2-10° C.

In still another embodiment of the present invention, the said drink is having the following characteristics:
  a) free from fishy odor;
  b) resembles coconut water in appearance and taste;
  c) stable at an ambient temperature and preferably in the range of 2-10 degree C.

The present invention is based on the following points:
a) Conceiving the idea that the sap of *Kappaphycus alvarezii* which, as disclosed in the prior art, is rich in potassium and several other minerals, can serve as a raw material for a nutritious drink.
b) Reasoning thereafter that, although the sap as such is unpalatable, it may be possible to make it palatable by removing objectionable odor, by improving its taste and by improving its aesthetic appearance.
c) Thereafter devising mostly physical methods of treatment of the sap to realize the objectives of (b) above while retaining the naturalness of the drink.
d) Attributing the unpalatable nature of the sap even after purification to excessive concentrations of salts and thereafter appropriately adjusting the taste with water and sweetener to produce a refreshing and palatable drink bearing resemblance to tender coconut water.
e) Extending the shelf life of the sap through use of suitable food grade preservatives and more preferably through non-chemical means of preservation.
f) Recognizing that residuals from the process of purification of sap would also find applications as plant nutrients.

The following examples are given by way of illustration of the present invention and should not be construed to limit the scope of present invention

EXAMPLE 1

25 Kg of 45 day old *Kappaphycus alvarezii* plants were freshly harvested in the month of August from CSMCRI's experimental cultivation site at Okha seacoast, Gujarat, India. 18.0 kg of sap was obtained after filtering over muslin cloth as disclosed in U.S. Pat. No. 6,893,479. The residue was kept aside for preparation of kappa carrageenan. After addition of preservative (1 g benzoic acid per liter of sap) the crude sap, which still contained finely suspended solids, was centrifuged at 10,000 rpm (15900×g force) for 30 minutes. A clear supernatant with pinkish hue was obtained which had an unpalatable fishy odor.

EXAMPLE 2

The crude sap obtained as described in Example 1 was treated with different amounts (400-1000 ppm) of alum in aqueous solution form. Facile settling was observed after 3 h with 1000 ppm alum whereas the settling time was 15 h with 400 ppm alum.

EXAMPLE 3

20 Kg of *Kappaphycus alvarezii* seaweed was harvested from Mandapam coast, which yielded 15 liters of sap following the method of Example 1. After adding 1 g/L of benzoic acid preservative, the crude sap was centrifuged at 8000 rpm and then passed through a 5μ polypropylene wound cartridge filter. 7 L of the treated sap, which had a faint yellowish, was diluted with 21 L of water containing 6% sucrose and 1 g/L benzoic acid. The resultant product was carbonated and served cold to a test audience that had assembled for an algology symposium.

EXAMPLE 4

The sap of Example 3 was passed through polysulfone-based ultrafiltration membrane cartridge having molecular weight cut off of 2,50,000 Dalton (0.05-0.06μ pore size). The resultant sap was completely colorless and the fishy odour was nearly absent though not completely eliminated.

EXAMPLE 5

The sap of Example 3 was passed through a carbon filter cartridge and thereafter through the UF membrane cartridge of Example 4. A colorless sap without any fishy odour was obtained. The sap was then diluted with sweetened water as described in Example 3 and feedback was once again sought from institute staff and visitors to the institute. The drink was found to be tasty and refreshing and several respondents indicated that the drink is similar in taste to tender coconut water. Nutritional data of this product is given in Table 1 below.

TABLE 1

Nutritional Data of the Drink of Example 5 served to people[a]

| Nutrient | Amount Present | Nutrient | Amount Present |
| --- | --- | --- | --- |
| Moisture | 97.62 g/100 ml | Iron | 0.017 mg/100 ml |
| Protein | 0.019 g/100 ml | Manganese | 0.004 mg/100 ml |
| Fat | 0.0008 g/100 ml | Nickel | 0.35 mg/100 ml |
| Crude Fibre | 0.0 g/100 ml | Copper | 0.003 mg/100 ml |
| Carbohydrate | 1.205 g/100 ml | Zinc | 0.011 mg/100 ml |
| Energy | 4.90 Kcal/100 ml | Chromium | 0.250 μg/100 ml |
| Sodium | 8.28 mg/100 ml | Lead | 0.081 μg/100 ml |
| Potassium | 73.52 mg/100 ml | Thiamine | 0.023 mg/100 ml |
| Magnesium | 98.85 mg/100 ml | Riboflavin | 0.010 mg/100 ml |
| Phosphorous | 1.50 mg/100 ml | B-Carotene | 0.0 mg/100 ml |
| Calcium | 5.66 mg/100 ml | Iodine | 54 μg/100 ml |

[a]Data coutesy National Institute of Nutrition, Hyderabad, India

EXAMPLE 6

Freshly liquefied seaweed was filtered crudely using cloth and preservative was incorporated into the sap. 4 L of the crude turbid sap, having an obnoxious fishy smell, was taken in the feed tank of an experimental set up made of food grade stainless steel. The sap was treated for 0.5 h with varying doses (0.0 to 1.0% w/v) of activated charcoal (Merck (India) Ltd.; sieved through mesh 200 and dried at 100° C. for one hour). The sap was then filtered through a 19-channel ceramic MF element (KM/B18/19C/45) with 0.054 m$^2$ filtration area, by slowly increasing the transmembrane pressure to 1.0 kg/cm$^2$ while maintaining the feed tank temperature at 12° C. with a chiller. The turbidity of the membrane filtered sap varied depending on the pretreatment with activated charcoal. Optimum results were obtained with 0.5% activated charcoal added in a single lot. The permeate flux was 9.1 L/m$^2$/h. The data for feed and permeate are given in Table 2 below.

TABLE 2

Physico-chemical data of crude sap and permeate of Example 6

| Sample | Turbidity (NTU) | TDS (ppm) | Conductance (ms/cm) | pH |
| --- | --- | --- | --- | --- |
| Crude Sap | 1927 | 36,000 | 71.1 | 3.9 |
| Permeate | 0.645 | 33,900 | 57.4 | 5.0 |

As can be seen from Table 2, the crude sap having cloudy appearance and obnoxious fishy smell gave way to a clear permeate having pale green hue and the aroma of tender green coconut, while the salt content remained virtually unchanged as evident from the TDS (total dissolved solids) data in the table above. Nutritional data of permeate is provided in Table 3. It can be diluted with sweetened water and served as drink.

TABLE 3

Nutritional Data of the Permeate of Example 6[a]

| Nutrient | Amount Present | Nutrient | Amount Present |
| --- | --- | --- | --- |
| Moisture | 94.38 g/100 ml | Iron | 8.58 mg/100 ml |
| Protein | 0.085 g/100 ml | Manganese | 0.22 mg/100 ml |
| Fat | 0.0024 g/100 ml | Nickel | 0.35 mg/100 ml |
| Crude Fibre | 0.0 g/100 ml | Copper | 0.077 mg/100 ml |
| Carbohydrate | 1.800 g/100 ml | Zinc | 0.474 mg/100 ml |
| Energy | 7.54 Kcal/100 ml | Chromium | 3.50 μg/100 ml |
| Sodium | 18.10 mg/100 ml | Lead | 0.51 μg/100 ml |
| Potassium | 358.35 mg/100 ml | Thiamine | 0.023 mg/100 ml |
| Magnesium | 116.79 mg/100 ml | Riboflavin | 0.010 mg/100 ml |
| Phosphorous | 2.96 mg/100 ml | B-Carotene | 0.0 mg/100 ml |
| Calcium | 32.49 mg/100 ml | Iodine | 160 μg/100 ml |

[a]Data coutesy National Institute of Nutrition, Hyderabad, India

Advantages:
  1. The present sap is on refining and preservation resembles coconut water in appearance and is free from fishy odor.
  2. The present sap can be packed in glass bottles or plastic bottles or sealed pouches or in large closed containers made of stainless steel or plastic.

3. The residue from which the sap is separated yields kappa carrageenan to the same extent as that obtained from dry seaweed prepared from equivalent weight of fresh seaweed as disclosed in the prior art.
4. By-product retentate stream is obtained after membrane filtration of the sap which can be used as plant nutrient.
5. Nutritious drink and liquid plant nutrient are obtained in addition to kappa carrageenan by the said process.
6. The production cost of said sap is less than 0.25 USD per liter when crude sap cost is 0.07 USD which cost assumes fresh seaweed price of 0.50 USD per ton based on price of 500 USD per ton of dry *Kappaphycus alvarezii*, fresh seaweed weight to dry seaweed weight of 10:1, 70% (w/w) recovery of sap from fresh seaweed, and loading of entire cost of fresh seaweed on sap alone.
7. The said drink can be produced to the extent of 2-4 million servings of 100 mL each per hectare of cultivation on rafts in the open sea assuming conservative estimate of 100 tons of fresh weight of tender *Kappaphycus alvarezii* per hectare.
8. The present drink can be produced in large volumes using present and afforded by the common man.
9. The present process of preparation of refined seaweed sap for edible purposes may be applicable to other seaweeds containing nutritious sap.
10. The present drink is refreshing, tasty and nutritious which is able to fulfill of daily requirements of all the essential micronutrient including iodine.

We claim:

1. A sterilized refreshing and tasty drink consisting essentially of the following ingredients:
    a) 2500-5000 mg/L potassium, 1000-2000.mu.g/L iodine and essential minerals selected from the group consisting of 150-200 mg/L sodium, 750-1250 mg/L magnesium, 250-350 mg/L calcium, 25-35 mg/L phosphorous, 50-100 mg/L iron, 3-6 mg/L zinc, and 1.5-2.5 mg/L manganese;
    b) 0.75-1.0 g/L protein, 15-25 g/L carbohydrate, 0.2-0.3 ppm thiamine, 0.1-0.2 ppm riboflavin and only traces of fat with total energy content of 70-100 Kcal/L;
    c) <6.mu.g/L lead and <40.mu.g/L chromium and
    d) preservatives having a concentration in the range of 0.2-0.4% (w/v) selected from the group consisting of benzoic acid, potassium benzoate, sodium benzoate and methyl paraben, optionally adding commercially available drinks, flavors or ingredients selected from the group consisting of salt, lime, herbs, spices, and carbon dioxide to the drink, wherein the refreshing and tasty drink is prepared from a processed sap obtained from marine algae *Kappaphycus alvarezii*.

2. A method for the preparation of a refreshing and tasty drink from marine algae *Kappaphycus alvarezii*, said method consisting essentially of the steps of:
    a) providing sap from *Kappaphycus alvarezii*;
    b) preservatives having a concentration in the range of 0.2-0.4% (w/v) selected from the group consisting of benzoic acid, potassium benzoate, sodium benzoate, methyl paraben and propyl paraben either alone or in combination to the sap obtained from step (a);
    c) treating the sap obtained from step (a) or step (b) with activated charcoal powder or carbon filter to remove fishy odor and improve palatability; and
    d) subjecting the sap obtained from step (c) to membrane filtration to remove colloidal impurities resulting in a permeate and a retentate, said membrane being selected from the group consisting of a polysulfone ultrafiltration membrane having a 200-300 kilodalton cut-off or a 19-channel ceramic microfiltration element, followed by sterilization carried out with heat, radiation or ozonlysis of the permeate to separate out all invisible microorganisms and to obtain the desired drink;
    said drink consisting essentially of:
    1) 2500-5000 mg/L potassium, 1000-2000.mu.g/L iodine and essential minerals selected from the group consisting of 150-200 mg/L sodium, 750-1250 mg/L magnesium, 250-350 mg/L calcium, 25-35 mg/L phosphorous, 50-100 mg/L iron, 3-6 mg/L zinc, and 1.5-2.5 mg/L manganese;
    2) 0.75-1.0 g/L protein, 15-25 g/L carbohydrate, 0.2-0.3 ppm thiamine, 0.1-0.2 ppm riboflavin and only traces of fat with total energy content of 70-100 Kcal/L; and
    3) <6 .mu.g/L lead and <40 .mu.g/L chromium,
    e) optionally adding commercially available drinks, flavors, or ingredients selected from the group consisting of salt, lime, herbs, spices, and carbon dioxide to the drink obtained from step d) through blending to enhance the taste of the drink.

3. The method as claim in claim 2, wherein a by-product retentate stream obtained after membrane filtration is useful as a plant nutrient.

4. The method as claimed in claim 2, wherein said drink has the following characteristics:
    a) free from a fishy odor;
    b) resembles coconut water in appearance and taste; and
    c) stable at ambient temperature in the range of 2-10 degree C.

* * * * *